(12) United States Patent
Martin et al.

(10) Patent No.: US 8,433,111 B2
(45) Date of Patent: Apr. 30, 2013

(54) METHOD FOR IMAGE DATA RECORDING WITH A MEDICAL MODALITY DESIGNED FOR IMAGE DATA RECORDING AND ASSOCIATED MEDICAL MODALITY

(75) Inventors: Diana Martin, Herzogenaurach (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1192 days.

(21) Appl. No.: 12/076,611

(22) Filed: Mar. 20, 2008

(65) Prior Publication Data
US 2008/0243759 A1    Oct. 2, 2008

(30) Foreign Application Priority Data
Mar. 21, 2007   (DE) .......................... 10 2007 013 566

(51) Int. Cl.
*G06F 17/30*   (2006.01)
*A61B 5/00*   (2006.01)

(52) U.S. Cl.
USPC .......................................................... 382/128

(58) Field of Classification Search .................. 382/128; 707/736
See application file for complete search history.

(56) References Cited

U.S. PATENT DOCUMENTS

| | | | | |
|---|---|---|---|---|
| 5,452,416 A | * | 9/1995 | Hilton et al. .................. | 715/783 |
| 6,473,717 B1 | * | 10/2002 | Claussen et al. .............. | 702/153 |
| 6,687,329 B1 | * | 2/2004 | Hsieh et al. ..................... | 378/62 |
| 6,973,162 B2 | * | 12/2005 | Block et al. ..................... | 378/63 |
| 6,988,074 B2 | * | 1/2006 | Koritzinsky et al. .............. | 705/2 |
| 7,162,004 B2 | | 1/2007 | Inoue et al. | |
| 7,263,710 B1 | * | 8/2007 | Hummel et al. ................. | 725/86 |
| 7,574,452 B2 | * | 8/2009 | Keen .................................... | 1/1 |
| 7,639,780 B2 | * | 12/2009 | Minyard et al. ................. | 378/37 |
| 7,936,908 B2 | * | 5/2011 | Brackett ...................... | 382/128 |
| 2004/0030246 A1 | | 2/2004 | Townsend et al. | |
| 2004/0117124 A1 | * | 6/2004 | Kiros et al. ..................... | 702/19 |
| 2004/0141661 A1 | * | 7/2004 | Hanna et al. .................. | 382/305 |
| 2004/0148403 A1 | * | 7/2004 | Choubey et al. .............. | 709/228 |
| 2004/0153862 A1 | * | 8/2004 | Grellmann et al. ............. | 714/43 |

(Continued)

FOREIGN PATENT DOCUMENTS

| | | |
|---|---|---|
| DE | 10346410 A1 | 5/2005 |
| DE | 102004052478 A1 | 6/2005 |

(Continued)

OTHER PUBLICATIONS

Microsoft Windows ME screenshot.*

(Continued)

*Primary Examiner* — David A Vanore
*Assistant Examiner* — Wyatt Stoffa
(74) *Attorney, Agent, or Firm* — Harness, Dickey & Pierce, P.L.C.

(57) ABSTRACT

A method for image data recording with a medical modality is provided. Protocols for image data recording using the at least two different image recording techniques are provisioned in a common database. The protocols are organized on the basis of body regions and/or clinical pictures. A body region and/or a clinical picture are selected and at least one protocol is displayed as a function of the selection. At least one display protocol for image data recording from the database is selected by a user and/or automatically, and image data is recorded as a function of the at least one selected protocol.

29 Claims, 2 Drawing Sheets

U.S. PATENT DOCUMENTS

| | | | |
|---|---|---|---|
| 2004/0167800 A1* | 8/2004 | Chang et al. | 705/2 |
| 2006/0025673 A1* | 2/2006 | De Leon et al. | 600/410 |
| 2006/0052685 A1* | 3/2006 | Cho et al. | 600/407 |
| 2006/0064318 A1* | 3/2006 | Alsafadi et al. | 705/2 |
| 2006/0184014 A1 | 8/2006 | Pfeiler | |
| 2007/0014489 A1* | 1/2007 | Sun et al. | 382/294 |
| 2007/0038070 A1 | 2/2007 | Tank | |
| 2007/0041623 A1* | 2/2007 | Roehrig et al. | 382/128 |
| 2007/0130165 A1* | 6/2007 | Sjoblom et al. | 707/10 |
| 2007/0272868 A1 | 11/2007 | Krieg et al. | |
| 2007/0286525 A1* | 12/2007 | Mahesh et al. | 382/276 |
| 2008/0097187 A1* | 4/2008 | Gielen et al. | 600/409 |
| 2008/0214927 A1 | 9/2008 | Cherry et al. | |
| 2009/0161927 A1* | 6/2009 | Mori et al. | 382/128 |
| 2010/0215225 A1* | 8/2010 | Kadomura et al. | 382/128 |
| 2011/0103551 A1* | 5/2011 | Bal et al. | 378/65 |

FOREIGN PATENT DOCUMENTS

| | | |
|---|---|---|
| DE | 102005011151 A1 | 10/2005 |
| DE | 102004039680 A1 | 11/2005 |
| DE | 102004058122 A1 | 7/2006 |
| DE | 102006015749 A1 | 10/2007 |
| JP | 2002-263088 A | 9/2002 |
| JP | 2006-055432 A | 3/2006 |
| JP | 2006-075596 A | 3/2006 |
| JP | 2006-081887 A | 3/2006 |
| JP | 2006-334294 A | 12/2006 |
| JP | 2006-346056 A | 12/2006 |
| WO | WO 2006/119085 A2 | 11/2006 |

OTHER PUBLICATIONS

German Office Action dated Sep. 20, 2010.

* cited by examiner

METHOD FOR IMAGE DATA RECORDING WITH A MEDICAL MODALITY DESIGNED FOR IMAGE DATA RECORDING AND ASSOCIATED MEDICAL MODALITY

PRIORITY STATEMENT

The present application hereby claims priority under 35 U.S.C. §119 on German patent application number DE 10 2007 013 566.3 filed Mar. 21, 2007, the entire contents of which is hereby incorporated herein by reference.

BACKGROUND

1. Field

Embodiments of the present invention relate to methods for image data recording with a medical modality, which is designed for image data recording by way of at least two different image recording techniques, and to an associated medical modality.

2. Description of the Conventional Art

Recently, so-called "hybrid modalities" in which different image recording techniques are combined have been increasingly used for medical imaging. One example of a modality such as this is a modality which allows both positron-emission tomography (PET) and computed tomography (CT) to be carried out. Further options for "hybrid modalities" such as these are represented by modalities which, for example, combine the image recording technique of computed tomography (CT) and single-photon-emission computed tomography (SPECT), as well as modalities for combining magnetic resonance imaging (MRI) and positron-emission tomography (PET), as well as magnetic resonance imaging and single-photon-emission computed tomography.

"Hybrid modalities" such as these generally use combinations of image recording techniques in which, on the one hand, a first image recording technique allows high spatial resolution, such as magnetic resonance imaging or computed tomography, while, on the other hand, the second image recording technique provides high sensitivity (such as nuclear medicine, for example in the configuration of SPECT or PET). One particularly suitable configuration is represented by the combination of magnetic resonance imaging with positron-emission tomography. However, of course, other combinations of image recording techniques are likewise possible and/or used in a "hybrid modality", possibly even combinations with more than two image recording techniques. The extent to which a modality such as this does or does not form a physical unit with respect to the various techniques is of only secondary importance to the fundamental principle of combination of image recording techniques.

If image recording is intended to be carried out using a "hybrid modality" such as this, then, in the case of the systems that exist now, and/or the prototypes, the image protocols and/or examination protocols for a patient are examined separately from one another for the various image recording techniques. For example, a PET protocol in conjunction with a plurality of MRI protocols are each selected separately for the recording technique in question. This selection and/or the organization of the procedure are/is in general carried out in this case by a medical/technical assistant or some other technician or scientist who is carrying out or monitoring the image recording process.

However, protocol selection is comparatively complex since the protocols depend not only on the diagnostic question but also on one another. For example, it is not possible to combine every magnetic resonance record with one or each positron-emission tomography record. Similar relationships exist for other recording techniques.

The medical/technical assistants and other technicians or scientists who carry out image recording in clinics are, however, generally trained for only one image recording technique. For example, they have experience either in nuclear medicine or in magnetic resonance imaging. It is, however, very rare for them to be entrusted with both image recording techniques. This makes the choice of the appropriate protocols and in particular their matching to one another very difficult. In some circumstances, incorrect combinations of examination protocols and image recording protocols produce inadequate image data records or insufficient quality (e.g., quality requirements are not met). In this case, repetition of individual recordings, which place stress on the patient, may be necessary.

DE 10 2004 039 680 A1 describes a method for carrying out the measurements using imaging medical examination facilities, with a plurality of examination facilities being controllable by way of a plurality of control consoles with equal authority. The image recording settings are made by the respective operators themselves.

DE 10 2005 011 151 A1 discloses a medical imaging diagnosis apparatus which comprises a PET gantry and a CT gantry. For data recording, the patient is automatically moved on a couch firstly through the PET examination facility and then through the CT examination facility.

DE 10 2004 052 478 A1 discloses a hybrid modality which allows magnetic resonance recording and X-ray recording.

US 2004/0030246 A1 describes a hybrid modality which has a PET and CT imaging facility. An attenuation correction factor is calculated from the images recorded by way of CT, and is included as a parameter in the PET image recording.

DE 10 2004 058 122 A1 discloses a method which allows images recorded by way of different image recording techniques to be registered together with one another. This is done by introducing landmarks into a CT image and PET image at the same time, in order to achieve accurate positional association.

SUMMARY

Embodiments of the present invention are based on the object of specifying a method, which is better in the context of image data recording with "hybrid modalities", which in particular assists and/or simplifies protocol selection, particularly with regard to combinations of protocols.

The following steps are intended to achieve this object for a method of the type mentioned initially:

provision of protocols for image data recording by way of the at least two different image recording techniques in a common database with the protocols being provided organized on the basis of body regions and/or clinical pictures, user selection of a body region and/or of a clinical picture, and display of at least one protocol on an image output means as a function of the selection, selection of at least one display protocol for image data recording from the database by a user and/or automatically, and image data recording as a function of the at least one selected protocol.

According to at least one embodiment of the present invention, the protocols for the examinations and/or image recording processes using the two image recording techniques are no longer separate, but are provided in a common database.

This database has different database functionalities, in particular the normal database functionalities, for example, appropriate links initially exist between the data items, that is to say the data is available in a structured form.

In one embodiment, for example, for image recording with the "hybrid modality", the protocols are stored such that, for example, the possible and worthwhile combinations are contained and/or preset in the appropriate tables in the database without an operator (e.g., a medical/technical assistant) himself requiring detailed knowledge relating to this. The database is appropriately configured for this purpose, for example, by an appropriate service provider for the "hybrid modality". The configuration and administration may also possibly be carried out by an administrator, trained for this purpose, in a clinic.

The protocol or plurality of protocols for image data recording using the "hybrid modality", that is to say using at least two different image recording techniques, is or are selected from the database by an operator or automatically.

Automatic selection can be carried out by way of appropriate software in conjunction with the database. This software and/or the database can be provided on a console for carrying out image recording. If required, the selection may be made by an operator, for example, based on automatic selection or preselection from the database, taking account of the relationships in the database. In this sense, a combination of selection by an operator with automatic selection is also feasible. It is likewise feasible for the operator to manually select the desired recording protocol or the plurality of recording protocols, following which a check is carried out on the basis of the data which is shared by the various image recording techniques and the database, thus subsequently indicating to the operator whether the selected type of image data recording is or is not worthwhile, and/or which specific settings are required for the selected protocols.

The protocols can be stored organized in the database such that image recording using the two different or the plurality of different image recording techniques is initiated by way of just one protocol. Common protocols can therefore be provided, for example, for magnetic resonance recording and positron-emission tomography recording. It is also feasible for the protocol for the respective image recording technique to be searched for separately. In this case, at least two protocols must be selected for one image data record such that the at least two image recording techniques are carried out combined.

The image data recording is carried out as a function of the at least one selected protocol automatically on the basis of the protocol selection, or with operator assistance. The selected protocol or the selected protocols is or are therefore used in order to carry out image data recording using the "hybrid modality". This image data recording may, in this case, be controlled via an appropriate console, in which the database is also stored.

The common database for the various image recording techniques therefore provides important assistance for combined protocol planning for "hybrid modalities". The database combines the data for image data recording with all the various recording techniques which are available for the medical modality. This suppresses and/or avoids the need for the previously required complex searching for protocols jointly in different databases for the respectively different image recording techniques. Furthermore, the structuring that is necessarily provided in a database allow organized protocol access.

According to embodiments of the present invention, the database may be stored in a console, which is designed for patient registration and/or control of the image data recording by way of the at least two different image recording techniques, of the medical modality, and/or is provided for this to access.

Consoles for imaging medical modalities are used, inter alia, to carry out image data recording and for patient registration—that is to say for inputting the name and the desired examination—and the like. In a method according to an embodiment of the present invention, the database is stored in a console, which is in the form of a common console for image data recording using the various image recording techniques. This allows the entire image data recording process to be controlled by a single console.

Duplicated patient registration is likewise avoided if the console allows registration for both image recording techniques. The image data recording process is therefore considerably simplified by the use of a single console for the "hybrid modality" or in the "hybrid modality". This avoids duplicated data inputs, which are necessarily subject to errors. Alternatively, a single console can be provided in which the database is not stored directly, but has access to it. In this case, for example, the database may be provided via an Intranet or the Internet, possibly by an external service provider, who also carries out the updating of the database, that is to say, for example, the inclusion of further image recording techniques or protocol updating.

According to at least one embodiment of the present invention, only one console need be used in order to carry out the image recording and to register the patient.

The protocols, data and/or selection fields associated with them can be displayed by way of a software interface on an image output means. Thus, for example, the single console of the "hybrid modality" in this case has appropriate software or has access to software whose interface allow the protocols and/or the data associated with them to be displayed. The expression "data" of the protocols should in this case be understood as meaning that, for example, a specific name for a protocol or a summary of the content is displayed on a screen or monitor, or the like. If required, appropriate selection fields for the individual protocols can be displayed. These may be text fields or fields with pictograms and the like, which refer to an appropriate protocol. If required, the protocol itself could also be displayed, that is to say for example not only a name but a specific procedure for image data recording that is being carried out. In this case, the protocols and/or the associated data are/is advantageously displayed in such a way that the relationships which must be taken into account in a select recording are imaged and/or can be called up.

At least one protocol for image data recording by way of positron-emission tomography, computed tomography, single-photon-emission computed tomography, magnetic resonance imaging, and/or X-ray based techniques may be provided in the database. It is, of course, likewise feasible for the database to contain further protocols for image recording techniques that have not been mentioned here. In particular, an adequate selection must be provided for all the image recording techniques of the "hybrid modality".

The protocols in the database are in this case configured such that they either allow data recording using a specific image recording technique or represent directly combined protocols, by way of which image data recording can be carried out using different image recording techniques, possibly using all of the various image recording techniques, in the "hybrid modality". If required, when different techniques are combined in one protocol, this is specifically suitable or intended for a specific diagnostic question or for a specific area to be imaged.

The protocols can be provided in a tree-like structure.

The protocols therefore are, or have been, associated with body regions and/or clinical pictures. This is achieved, for example, by way of appropriate different levels for selection which, in particular, are provided on a software interface. For example, it is feasible to allow a specific body area of the patient or a specific examination area to be specified on a first level for selective purposes. For this purpose, an operator can be provided with a complete overview or an overview which has already been restricted and, for example, has been produced as a function of a patient registration process that has taken place, by access to the patient files. In this case, for example, the operator selects the area of the abdomen for image data recording. A second level, inter alia, can then be opened in a tree structure, or a new page or a new window can be opened in the software, which provides the selection interface, providing a capability for more detailed selection.

By way of example, the abdominal organs can be displayed on this selection level. On a further, third level, specific illnesses or clinical pictures can be displayed after appropriate selection, which are typical or occur frequently for this organ, with the associated examination protocols being displayed after selection or in parallel with the appropriate clinical pictures. In this case, the examination protocols for the various image recording techniques are advantageously displayed as combination protocols and visually on the software interface, linked in such a way that the operator can see that it is worthwhile linking these two protocols or a plurality of protocols displayed in an appropriately linked form.

The protocols are accordingly and expediently provided taking account of the relationships which are governed by the at least two image recording techniques. The protocol provision process is therefore carried out in such a way that specific relationships, which must be taken into account by the combination of a plurality of image recording techniques, are considered. By way of example, the only protocols and/or the only data associated with these protocols that are/is displayed is that which can be combined in a worthwhile form for a desired examination, or in general for a combination of the two image recording techniques. This is done by accessing the structure of the database. For example, this results in an operator being offered a plurality of magnetic resonance protocols, for example, in the form of appropriate text fields, for selection, with the display being provided in such a way that a positron-emission protocol, which can be combined well with these magnetic resonance protocols, is likewise offered for selection, that is to say by way of example they are displayed adjacent, or offered for selection after selection of the corresponding magnetic resonance protocols, or are automatically associated.

The relationships for recording of positron-emission image data may include the requirement for a previous magnetic resonance image data record to allow calculation of an attenuation correction, and/or the requirement to record the magnetic resonance scout image data for (detailed) planning of an image data recording by way of positron-emission tomography and/or a relationship between a reconstruction volume for the positron-emission tomography of measurement field changes during a magnetic resonance image data recording and/or a definition of automatic multiplanar reconstructions of positron-emission image data by way of two-dimensional magnetic resonance image data.

Consideration is therefore given, for example, to the possibility that a previous magnetic resonance record may be required in order to calculate the attenuation correction for positron-emission measurements. The joint database therefore allows a user to use image relationships such as these to combine the appropriate protocols, offer them directly in a joint recording protocol, or select them automatically after they have been appropriately provided by the database.

Furthermore, magnetic resonance scout recordings may be required for detailed planning of positron-emission tomography recording. Scout recordings such as these are accordingly added to the PET protocol, or are completed in it, directly when an operator is provided with the indication that a specific PET record is planned. Measurement field changes in magnetic resonance imaging can adapt the reconstruction volumes for the PET, two-dimensional protocols from magnetic resonance imaging may define corresponding automatic reconstructions of the PET data with respect to the various angles of the levels, etc. These relationships exist in the database and are imaged, for example, on an appropriate console interface or user interface.

Depending on any selection of at least one protocol that has already been made, the protocols can be provided in combinations and/or sequences, which are governed by the at least two different image recording techniques.

For example, depending on a selection of a PET protocol with a long measurement time for a specific body region with the aid of the common database, a magnetic resonance protocol with a relatively long measurement time and better image quality, instead of a protocol such as this with a short measurement time, may be provided for an operator for the second image recording technique, or this may be provided for this purpose from the database, since the examination time is in this case governed by the PET measurement anyway. Even if no protocol selection has yet been made, specific restrictions may govern the provision process which, for example, is governed solely by the combination of the various image recording techniques, such that the protocols are displayed accordingly, selected or preselected on this basis.

In particular, as already mentioned, a protocol with a comparatively long measurement time can likewise be provided for selection of a protocol for image data recording by way of positron-emission tomography with a long measurement time for image data recording in comparison to MRI for image data recording by way of magnetic resonance imaging.

A menu structure for selection of combinations of protocols and/or for sequencing them in time can be generated in one or more selection steps with the aid of the data in the database, and may be displayed for an operator on an image output means.

The display may be produced with the aid of the already mentioned software and its user interface. Advantageous protocol combinations can therefore be proposed directly in the form of a menu, for which purpose the software accesses the appropriate structure of the data in the database, possibly as well as further information, for suitable combinations, possibly in a further lower-level or separate database, in particular for the desired menu display and organization in selection steps. In consequence, not only are the protocols provided organized on the basis of body regions and/or clinical pictures, but a menu structure is produced directly which allows specific selection of protocol combinations, and the procedure for them. In this case, specific user guidance can be achieved by way of a plurality of selection steps, which follow one another and require interaction on each occasion.

The menu structure can be provided as a function of the selection and/or notification of at least one indication and/or clinical picture and/or body region by an operator. The menu structure, that is to say, in particular the specific configuration of a user interface of the software, which is displayed on a common console or the like, is thus generated and/or displayed as a function of an operator input. The selection by the operator may also relate to patient registration provided that access to the patient files is already linked to this registration process, in which files there may be a specific indication or a clinical picture which just needs to be accessed in this case.

By way of example, the operator can use an appropriate text field to provide an indication or to select one from a list of indications. For example, it is possible to state that entire-body staging or a search for metastases over the entire body of the patient is planned. In this case, a combination of protocols can be proposed automatically in the form of a menu by the software and/or using the database with its structuring, for example, in a PET protocol, the protocol T1 for magnetic resonance recording and the protocol STIR for producing magnetic resonance recordings of the entire body area.

In addition, a magnetic resonance prescan is carried out automatically in order to determine the data for the PET attenuation correction in accordance with a procedure plan. The sequence of the protocols or the procedure is optimized, for example, automatically with regard to the field of view for the individual levels and the table feed. The operator now still has the capability to confirm his agreement to the proposed procedure by using the displayed menu structure, if this is desired. Alternatively, the image data recording can also be started or initiated automatically.

The sequence and/or the procedure for the selected protocols can be optimized automatically in order to minimize the image data recording time. This can in turn be done as a function of a specific indication of a clinical picture or the like, by way of a computation device, in particular a common console and/or by way of the database. When magnetic resonance imaging is combined with PET measurements, this can be done, for example, such that the slice thickness and/or the number of magnetic resonance slices are matched to the PET measurements.

The slice thickness and the number of slices for a magnetic resonance image data recording are, in this case, matched to the planned image data recording by way of positron-emission tomography, for example in order to minimize the image data recording time.

If required, an operator can edit the database and/or add protocols and/or protocol combinations. Embodiments of the present invention therefore advantageously allow the database to be edited. This can be done by an operator (e.g., a medical/technical assistant, scientist, or the like who is monitoring the overall image recording process) in situ. It is likewise possible for the operator in this case to be an external service provider who makes changes to the database. Appropriate authorization or editing authorization can be provided if required.

By way of example, protocols can be added for a newly included image recording technique. Protocol combinations can likewise be newly created, for example with regard to examinations which have not previously been carried out or newly identified relationships and/or advantageous combinations. The capability to adapt and administer the database allows the image data recording with "hybrid modality" to be improved in steps as a function of the further development of technology in this field, and the specific requirements which exist in individual clinics and/or hospitals.

According to at least one embodiment of the present invention, further protocols can also be provided for selection during image data recording, possibly as a function of already recorded image data. For example, a proposal of a further protocol can occur if it is found—during the course of image data recording—that a PET measurement must be extended because fewer results have been detected per unit time than was originally expected. In this case, other advantageous magnetic resonance measurements may be proposed to the operator with an appropriately configured "hybrid modality".

If required, a proposal such as this for a further protocol may also be standard, so that the corresponding software for the console for controlling the "hybrid modality" makes it possible, during the examination, for an operator to select additional protocols by a single mouse click or some other selection option.

In particular, as already mentioned, further protocols may be provided for magnetic resonance image data recording and/or image data recording using a different image recording technique, as a function the number of events obtained while recording positron-emission image data.

The protocols can also be provided taking account of supplementary image data recording options, for example, gating of an image recording technique by a further image recording technique, and/or restrictions. This therefore takes account of additional options and features for image data recording which are possible and worthwhile in particular in conjunction with the two different image recording techniques or the plurality of different image recording techniques.

For example, a PET examination can be gated with the aid of a magnetic resonance navigator. In this context or else in the context of taking account of relationships, it is possible, for example, to reject data which is subject to smearing as a result of patient breathing motion. Furthermore, negative relationships for image data recording, that is to say image data recording restrictions, can be considered. For example, the image data recording can be limited by tracer half-lines. This allows additional image data recording options and restrictions to image data recording to be included and/or taken into account in the protocol provision.

Furthermore, at least one embodiment of the present invention relates to a medical modality designed for image data recording using or by way of at least two different image recording techniques, in particular in order to carry out a method as described above. The medical modality has a console designed for patient registration and/or control of the image data recording by way of the various image recording techniques. The medical modality also has a database, which is used jointly by the various image recording techniques, stored in the console and/or provided for access for this. The database stores protocols for image data recording by way of the image recording techniques.

The medical modality is accordingly provided with a single console, which can be used for patient registration and advantageously likewise to control image recording using a plurality of image recording techniques, that is to say using two or more image recording techniques, which are provided by the "hybrid modality". There is therefore no need to make different inputs on different consoles, as was the normal practice until now.

The common database on which the interface or user interface is based and which is provided to the operator on the console takes account of interactive relationships between the individual protocols for the various techniques. The protocols are displayed to an operator (e.g., a medical/technical assistant) on the single console of the "hybrid modality". This display may, for example, be in the form of a menu structure with a plurality of selection steps. For this purpose, the console may have an appropriate image output means, which the operator makes use of, with the aid of a control tool for the console, such as a keyboard, mouse or other input device.

The "hybrid modality" is designed such that the image data recording is carried out taking account of the relationships between the various image recording techniques. The image data recording is therefore optimized with respect to the fundamental protocols such that, for example, the examination duration is reduced and/or minimized and the combination of the various techniques is determined or predetermined in a worthwhile manner. If required, the selection may be made freely by an operator, in which case an appropriate selection is checked by the software in the console.

Thus, in principle, different image recording techniques are combined in a common, the same or a single protocol database, in particular for controlling the modality by way of a single associated console.

BRIEF DESCRIPTION OF THE DRAWINGS

Further advantages, features and details of the present invention will become evident from the following exemplary embodiments and from the drawings, in which.

DETAILED DESCRIPTION OF EXAMPLE EMBODIMENTS

Figure 1:
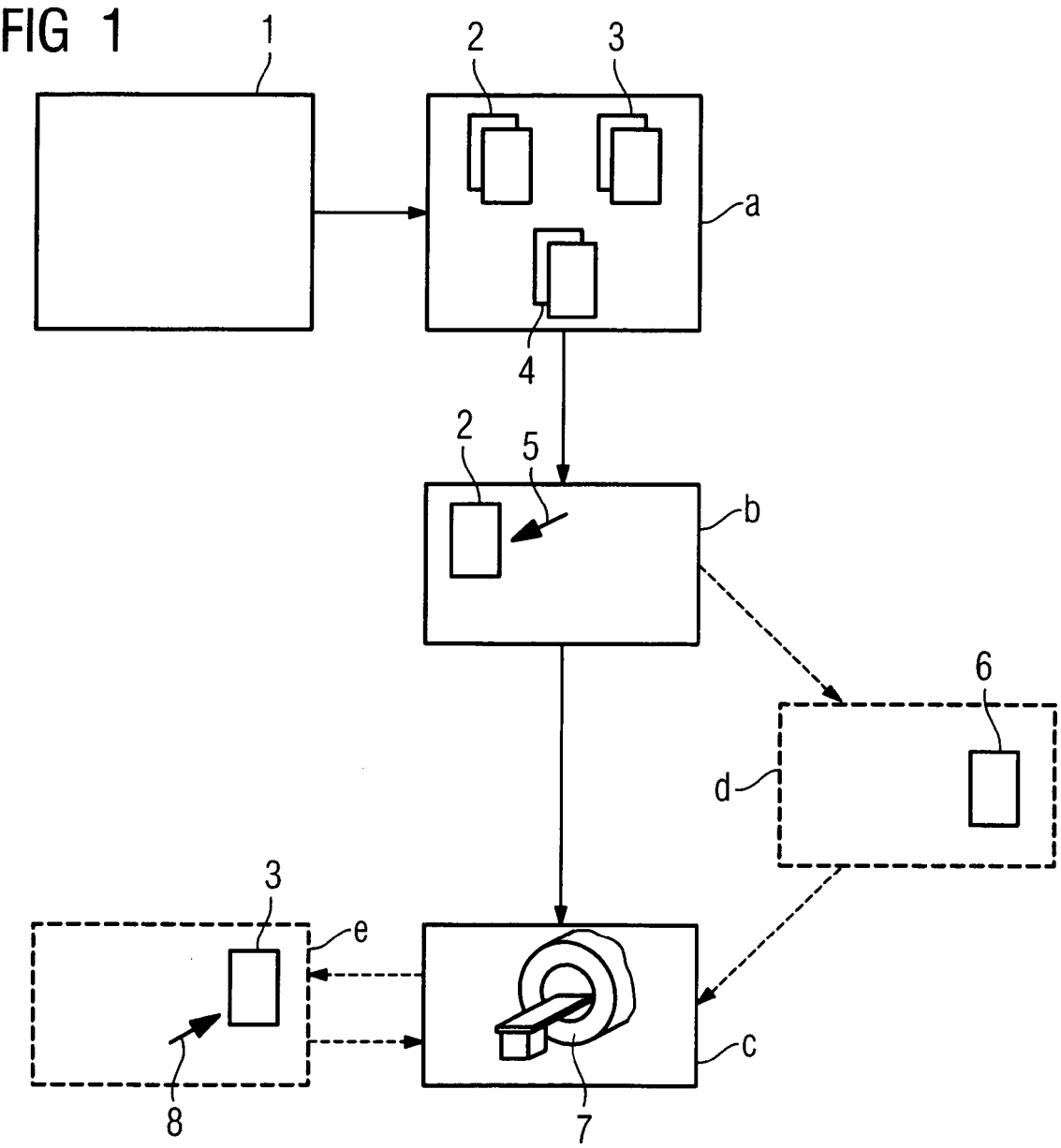
FIG. 1 shows a flowchart of a method according to an embodiment of the present invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a flowchart of a method according to an embodiment of the present invention, with the obligatory steps a-c.

In this case, first of all, in step a protocols 2, 3 and 4 are provided for the various image recording techniques from a database 1. The database 1 is used jointly for the various image recording techniques by the image recording modality of the method according to an embodiment of the present invention. This protocol provision can be provided on an image output means, which is not shown here, but on which, for this purpose, the designations of the protocols and the associated data for the protocols are advantageously displayed rather than the protocols themselves.

As shown in FIG. 1, the display may, for example, be in the form of selection fields. The protocols 2 and 3, which are indicated by appropriate small boxes here, are protocols for one or the other image recording technique for the medical modality that is used for the method, and which in the present case is a "hybrid modality" for two different image recording techniques. The protocols 4, which are likewise stored in the database 1, are combined protocols, as indicated by the central arrangement of the small boxes, that is to say integrated protocols for image recording using the two different image recording techniques. Therefore, in this case, image recording using two different image recording techniques is initiated by selection of a protocol 4. The protocols 2 and 3 may be selected in specific combinations by an operator who, for this purpose and by way of example, works with a control tool on a software interface or user interface on a control console for image data recording.

This selection of one or more protocols is indicated in step b. In this case, an operator has selected a protocol 2 with the aid of a control tool, which is in this case indicated by the mouse arrow 5. This selection as made by an operator here may be supported by automatic selection of protocols from the database. This automatic selection may, for example, be carried out as a selection or preselection as a function of an entered indication or the like, not illustrated here, and leads, for example, to a restricted number of protocols 2 and 3.

In addition to the protocol 2, which was selected in step b, a further protocol 6 can optionally be selected from the protocols 2, 3 or 4 in step d. This can be displayed to the operator on an appropriate software interface, for example, as a function of the selection, which has already been made of a protocol 2 in step b. In this case, the user once again clicks on the appropriate protocol 6, so that image data recording can be carried out as per step c.

It is likewise possible, following step b, for image data recording to be carried out directly as per step c, in which case the image data record is intended to be indicated here by a display of the "hybrid modality" 7. In order to exploit the advantages of the common database, a further protocol 3 or 4 should then be selected, initiating image data recording using the further image recording technique, or including the other imaged recording technique. In the present case, this is indicated by the optional step e, in which a protocol 3 is selected with the aid of a mouse arrow 8.

The advantage of the method according to at least this embodiment of the present invention is the common database 1 for the various image recording techniques, in which the protocols 2, 3 and 4 for these techniques are stored and can be called up. For example, this allows simple patient registrations and, in particular, protocol selections specifically for users who have little experience with one of the two modalities. For example, this advantageously allows medical/technical assistants from the field of nuclear medicine to use a common console to control "hybrid modalities" which are designed to create magnetic resonance recordings, without major difficulties and without having to call on a specialist for the other image recording technique. This is made possible by the common database 1, which holds the protocols for image data recording using two image recording techniques, in the structured form that is typical of databases, and allows information to be called up in an organized manner.

Figure 2:
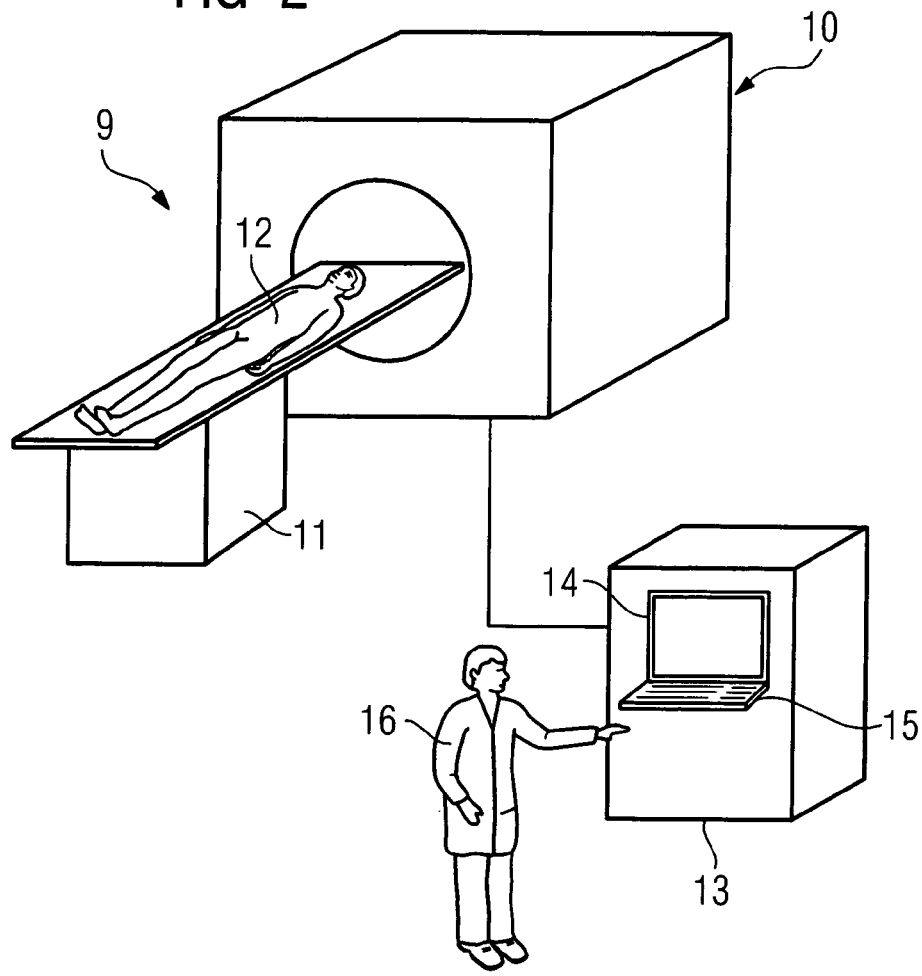
FIG. 2 shows a medical modality according to an embodiment of the present invention.

FIG. 2 shows a medical modality 9 according to an embodiment of the present invention which, in addition to an image recording apparatus 10 with a patient couch 11 on which a patient 12 is located, has a console 13 in which an image output means 14 with a control tool 15 is integrated. The console 13 is controlled by an operator 16.

In the case illustrated here, the image recording apparatus 10 is designed to record images by way of magnetic resonance imaging and positron-emission tomography.

The operator 16 now registers the patient 12 on the console 13, which is used jointly for the two image recording techniques of the image recording apparatus 10 for the medical modality 9. For this purpose, the console 13 has software with a database, in which examination protocols are stored for both image recording techniques of the image recording apparatus 10, or of the medical modality 9. The database and the software in this case map together the relationships between the image data recording under those techniques of the image recording apparatus 10. For example, the protocols are associated with body regions and clinical pictures in the form of a tree structure, which may be displayed for this purpose on the image output means 14.

The operator 16 is now guided through a menu, which is displayed on the image output means 14, as a function of the registration of the patient and, for example, an input of a clinical picture, and can use the control tool 15 to select the protocols for the image recording techniques. This protocol selection is, in this case, guided and structured by the structure of the database and the configuration of the associated software. The image output means 14 with the control tool 15 provide the operator 16 with the capability, possibly in a plurality of selection steps, to decide on the proposed advantageous protocol combinations or combined protocols. In this case, these are displayed in a structured from such that the time sequence is optimized and a desired reduced and/or minimum examination time can thus be achieved.

The image output means 14 also provides the operator 16 with the capability to edit and/or adapt the database for the console 13, for example, to add new protocol combinations for image data recording by way of the image recording apparatus 10. In consequence, even if the operator 16 has relatively little experience, particularly with one of the two image recording techniques, these ensure reliable and optimum image data recording.

Figure 3:
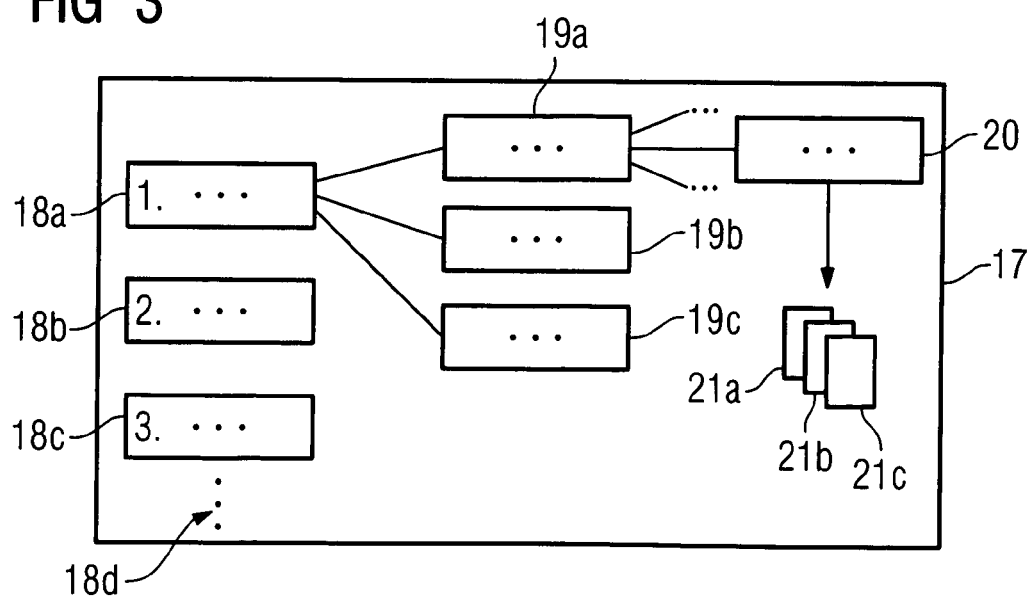
FIG. 3 shows an example of the provision of protocols for a method according to an embodiment of the present invention, illustrated on the basis of a menu structure on an image output means.

FIG. 3 shows an example of the provision of protocols for a method according to an embodiment of the present invention, illustrated on the basis of a menu structure 17 on an image output means. The protocols are organized by the basic database structure in the manner illustrated here, on the basis of the menu structure 17.

In this embodiment, the menu structure 17 is constructed in the form of a tree such that different selection levels are created by this type of provision for the user or operator.

In a first level, as shown by the small box 18a-18c, an operator is offered an overview of various body regions which are available for image data recording, and which may be more comprehensive than is illustrated here, as indicated by the small dots 18d.

For example, the text "pelvis" is reproduced for the appropriate body region in the small box 18a, while the text "head", is shown in the small box 18b, and the text "heart" in the small box 18c. The operator is therefore presented with various body regions for selection. Image displays can possibly be provided in addition to or alongside the text display of the individual body regions in the small boxes 18a-18c.

The operator makes a selection with the aid of the display on the image output means, by way of an appropriate control tool such as a computer mouse. Once the small box 18a for "pelvis" has been selected, the next level of the tree structure is opened, which once again comprises the small boxes 19a-19c and, possibly, further small boxes which are not illustrated here. By way of example, various chemical pictures for the area of the pelvis, which is to be selected by way of the small box 18a, are displayed in the small boxes 19a-19c. In the present case, the operator selects the small box 19a, in which, in the present case, the tumors in the pelvic area are provided for selection.

In a further branch in the tree structure, as shown in the small box 20, the operator selects prostate tumors, in response to which the menu structure 17 shows the protocols 21a-21c, all of which originate from the basic common database for the various image recording techniques and allow image recording using the various techniques in a sensible manner, for example as combination protocols for the various image recording techniques, so that prostate tumors can be optimally recorded. If required, the protocols 21a-21c may also be provided in a specific sequence, which can be adapted by the user if necessary, or is performed automatically, once the user has confirmed the proposed protocols 21a-21c, or has made a selection.

Even for an operator with only a small amount of experience related to one of the two image recording techniques, the database on which the protocols are based makes it possible to carry out image data recording in a worthwhile manner. Patient registration and image data recording are in this case advantageously carried out by way of a common console, thus considerably simplifying the control process.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

We claim:

1. A method for image data recording with a medical modality, which is designed for image data recording using at least two different image recording techniques, the method comprising:
provisioning image data recording protocols for at least two different image recording techniques in a common database, the protocols being organized on the basis of at least one of body regions and clinical pictures;
selecting at least one of a body region and a clinical picture;
displaying at least one protocol as a function of the selected at least one of the body region and clinical picture;
selecting at least one display protocol for image data recording from the database; and
recording image data as a function of the at least one selected protocol.

2. The method as claimed in claim 1, wherein the database is stored in a console, the console being designed for at least one of patient registration and control of the image data recording.

3. The method as claimed in claim 1, wherein at least one of the protocol, data, and selection fields associated with at least one of the protocol and data are displayed by a software interface on a display.

4. The method as claimed in claim 1, wherein at least one image data recording protocol for at least one of positron-emission tomography, computed tomography, single-photon-emission computed tomography, magnetic resonance imaging, and X-ray based techniques is provided in the database.

5. The method as claimed in claim 1, wherein the at least one protocol is provided in a tree-like structure.

6. The method as claimed in claim 1, further comprising:
providing the at least one protocol taking into account at least one relationship resulting from the at least two image recording techniques.

7. The method as claimed in claim 6, wherein the at least one relationship is at least one relationship for recording of positron-emission image data, the at least one relationship including at least one of,
a requirement for a previous magnetic resonance image data record to allow calculation of an attenuation correction,
a requirement to record a magnetic resonance scout image data for planning image data recording by positron-emission tomography,
a relationship between a reconstruction volume for the positron-emission tomography and measurement field changes during a magnetic resonance image data recording, and
a definition of automatic multiplanar reconstructions of positron-emission image data using two-dimensional magnetic resonance image data.

8. The method as claimed in claim 1, wherein the at least one protocol is provided as a function of a selection of at least one protocol in at least one of combinations and sequences, which are governed by the at least two different image recording techniques.

9. The method as claimed in claim 8, wherein a protocol with a long measurement time is provided for selection of a protocol for image data recording by positron-emission tomography, the positron-emission tomography having at least a long required measurement time in comparison to image data recording by magnetic resonance imaging.

10. The method as claimed in claim 1, the selecting of the at least one display protocol further comprises:
generating a menu structure to at least one of select and sequence combinations of protocols with the aid of the data in the database, and
displaying, for selection by an operator, the menu structure.

11. The method as claimed in claim 10, wherein the menu structure is provided as a function of at least one of the selection and notification, by an operator, of at least one of an indication and at least one of a clinical picture and a body region.

12. The method as claimed in claim 1, further comprising: automatically optimizing at least one of a procedure and a sequence for the selected at least one protocol.

13. The method as claimed in claim 12, wherein the automatically optimizing further comprises: matching a slice thickness and number of slices for a magnetic resonance image data record to an image data record by positron-emission tomography.

14. The method as claimed in claim 1, wherein an operator at least one of edits the database and adds at least one of protocols and protocol combinations to the database.

15. The method as claimed in claim 1, wherein at least one further protocol is provided for selection during image data recording, the at least one further protocol being provided as a function of already recorded image data.

16. The method as claimed in claim 15, wherein the at least one further protocol is provided for at least one of a magnetic resonance image data recording and an image data recording using a different image recording technique, the at least one further protocol being provided as a function of the number of decay events during the recording of positron-emission image data.

17. The method as claimed in claim 1, wherein the protocols are provided by taking account of supplementary image data recording options, the supplementary image data recording options including at least one of gating of an image recording technique by a further image recording technique, and restrictions.

18. A medical modality device designed for image data recording using at least two different image recording techniques, the medical modality device being configured to carry out a method as claimed in claim 1, the medical modality device comprising:
a console for at least one of patient registration and control of the image data recording using at least two image recording techniques, the console including a database stored therein, the database storing image data recording protocols for the at least two image recording techniques and being used jointly by the various image recording techniques.

19. The method as claimed in claim 2, wherein at least one of the protocol, data, and selection fields associated with at least one of the protocol and data are displayed by a software interface on a display.

20. The method as claimed in claim 2, wherein at least one image data recording protocol for at least one of positron-emission tomography, computed tomography, single-photon-emission computed tomography, magnetic resonance imaging, and X-ray based techniques is provided in the database.

21. The method as claimed in claim 3, wherein at least one image data recording protocol for at least one of positron-emission tomography, computed tomography, single-photon-emission computed tomography, magnetic resonance imaging, and X-ray based techniques is provided in the database.

22. The method as claimed in claim 2, wherein the at least one protocols are provided in a tree-like structure.

23. The method as claimed in claim 3, wherein the at least one protocols are provided in a tree-like structure.

24. The method as claimed in claim 4, wherein the at least one protocol is provided in a tree-like structure.

25. The method as claimed in claim 2, further comprising: providing the at least one protocol taking into account at least one relationship which results from the at least two image recording techniques.

26. The method as claimed in claim 25, wherein the at least one relationship is at least one relationship for recording of positron-emission image data, the at least one relationship including at least one of,
a requirement for a previous magnetic resonance image data record to allow calculation of an attenuation correction,
a requirement to record a magnetic resonance scout image data for planning image data recording by positron-emission tomography,
a relationship between a reconstruction volume for the positron-emission tomography and measurement field changes during a magnetic resonance image data recording, and
a definition of automatic multiplanar reconstructions of positron-emission image data using two-dimensional magnetic resonance image data.

27. A medical modality device designed for image data recording using at least two different image recording techniques, the medical modality device comprising:
means for provisioning image data recording protocols for at least two different image recording techniques in a common database, the protocols being organized on the basis of at least one of body regions and clinical pictures;
means for selecting at least one of a body region and a clinical picture;
means for displaying at least one protocol as a function of the selected at least one of the body region and clinical picture;
means for selecting at least one displayed protocol from the database; and
means for recording image data as a function of the at least one selected protocol.

28. A non-transitory computer readable medium including program segments for, when executed on a computer device, causing the computer device to implement the method of claim 1.

29. A medical modality device designed for image data recording using at least two different image recording techniques, the medical modality device comprising:
a console including a database to provision image data recording protocols for at least two different image recording techniques, the protocols being organized on the basis of at least one of body regions and clinical pictures, the console to select at least one of a body region and a clinical picture and to select at least one displayed display protocol from the database;
a display to display at least one protocol as a function of the selected at least one of the body region and clinical picture; and
an image recording apparatus to record image data as a function of the at least one selected protocol.

* * * * *

UNITED STATES PATENT AND TRADEMARK OFFICE
CERTIFICATE OF CORRECTION

PATENT NO. : 8,433,111 B2
APPLICATION NO. : 12/076611
DATED : April 30, 2013
INVENTOR(S) : Martin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1208 days.

Signed and Sealed this
Sixteenth Day of December, 2014

Michelle K. Lee
*Deputy Director of the United States Patent and Trademark Office*